(12) United States Patent
Maurits

(10) Patent No.: US 12,108,747 B2
(45) Date of Patent: Oct. 8, 2024

(54) LARGE-SCALE, HIGH DENSITY STORAGE OF LARVAE

(71) Applicant: Bühler AG, Uzwil (CH)

(72) Inventor: Petrus Maria Jansen Maurits, Bavel (NL)

(73) Assignee: Bühler AG, Uzwil (CH)

( * ) Notice: Subject to any disclaimer, the term of this patent is extended or adjusted under 35 U.S.C. 154(b) by 796 days.

(21) Appl. No.: 15/734,262

(22) PCT Filed: Jun. 5, 2019

(86) PCT No.: PCT/EP2019/064673
§ 371 (c)(1),
(2) Date: Dec. 2, 2020

(87) PCT Pub. No.: WO2019/234107
PCT Pub. Date: Dec. 12, 2019

(65) Prior Publication Data
US 2021/0212300 A1    Jul. 15, 2021

(30) Foreign Application Priority Data

Jun. 5, 2018 (EP) ..................................... 18175908

(51) Int. Cl.
*A01K 67/033* (2006.01)
(52) U.S. Cl.
CPC .................................. *A01K 67/033* (2013.01)
(58) Field of Classification Search
CPC .................................................. A01K 67/033
USPC .................................................. 119/6.5, 6.7
See application file for complete search history.

(56) References Cited

U.S. PATENT DOCUMENTS

| 4,765,275 A | * | 8/1988 | Yukawa ................. A01N 63/12 119/6.5 |
| 7,347,615 B2 | * | 3/2008 | van der Plas .......... A01K 5/004 366/314 |
| 8,025,027 B1 | * | 9/2011 | Morales-Ramos .. A01K 67/033 119/6.5 |

(Continued)

FOREIGN PATENT DOCUMENTS

| AU | 635921 B2 * | 4/1993 |
| CN | 201029375 Y * | 3/2008 |

(Continued)

OTHER PUBLICATIONS

Reliable and practical methods for cryopreservation of embryogenic cultures (https://www.sciencedirect.com/science/article/pii/S0011224017300615?via%3Dihub) (Year: 2017).*

(Continued)

*Primary Examiner* — Timothy D Collins
*Assistant Examiner* — Maria E Graber
(74) *Attorney, Agent, or Firm* — The Webb Law Firm

(57) ABSTRACT

The present invention provides a method for storing insect larvae by means of a storage means. The insect larvae are stored in a cooling medium, e.g. water, in the storage means. The amount of water in the larvae-water mixture in the storage means is controlled to be between 30% and 80%. The content of the storage means is maintained at a temperature below 15° C. The content of the storage means is agitated using agitating means included in the storage means.

8 Claims, 1 Drawing Sheet

(56) References Cited

U.S. PATENT DOCUMENTS

| | | | | |
|---|---|---|---|---|
| 11,357,218 | B2* | 6/2022 | Jansen | A01K 1/0082 |
| 11,638,410 | B2* | 5/2023 | Calis | A01K 1/0047 |
| | | | | 119/6.5 |
| 2011/0045141 | A1 | 2/2011 | Natori et al. | |

FOREIGN PATENT DOCUMENTS

| | | | | | |
|---|---|---|---|---|---|
| CN | 103141447 | A | * | 6/2013 | |
| CN | 103493789 | A | | 1/2014 | |
| CN | 203467453 | U | * | 3/2014 | |
| CN | 203923179 | U | | 11/2014 | |
| CN | 107372458 | A | * | 11/2017 | |
| FR | 2845244 | A1 | * | 4/2004 | A01K 61/008 |
| JP | 2829852 | B2 | * | 2/1998 | |
| JP | 200032873 | A | | 2/2000 | |
| JP | H10200373 | A | | 2/2000 | |
| KR | 100667859 | B1 | * | 1/2007 | |
| RU | 2154940 | C3 | | 8/2000 | |
| WO | WO-8601074 | A1 | * | 2/1986 | |
| WO | WO-2006057552 | A1 | * | 6/2006 | |
| WO | 2009139346 | A1 | | 11/2009 | |
| WO | 2015023178 | A1 | | 2/2015 | |

OTHER PUBLICATIONS

Effects of moisture content of food waste on residue separation, larval growth (https://www.sciencedirect.com/science/article/pii/S0956053X17304294?ref=pdf_download&fr=RR-2&rr=802853b33aef0f77) (Year: 2017).*

Storage of male Glossina palpalis gambiensis pupae (https://parasitesandvectors.biomedcentral.com/articles/10.1186/s13071-014-0465-y) (Year: 2014).*

Insect Diapause A Review Gill, H. K., Goyal, G., and Chahil, G. 2017. Journal of Agricultural Science and Technology A 7 454-473 doi: 10.17265/2161-6256/2017.07.002 (https://davidpublisher.com/Public/uploads/Contribute/5a5c6c5a389c3.pdf) (Year: 2017).*

Chen et al., "Feeding Technology of Aphidoletes Aphidimyza," Bulletin of Agricultural Science and Technology, 1988, p. 24, vol. 1988(8).

Balestrino et al., "Mosquito Mass Rearing Technology: A Cold-Water Vortex Device for Continuous Unattended Separation of Anopheles arabiensis Pupae from Larvae," 2011, J Am. Mosquito Control Association, vol. 27, No. 3, pp. 227-235.

Di Ciccio et al., "Digital Control of a Continuous Stirred Tank Reactor," 2011, Mathematical Problems in Engineering, vol. 2011, pp. 1-18.

Eigenberger et al., "Reactor stability and safe reaction engineering," 1989, International Chemical Engineering, vol. 29, No. 1, pp. 12-25.

Kostal et al., "Physiological basis for low-temperature survival and storage of quiescent larvae of the fruit fly *Drosophila melanogaster*," 2016, Scientific Reports., vol. 6, pp. 1-11.

* cited by examiner

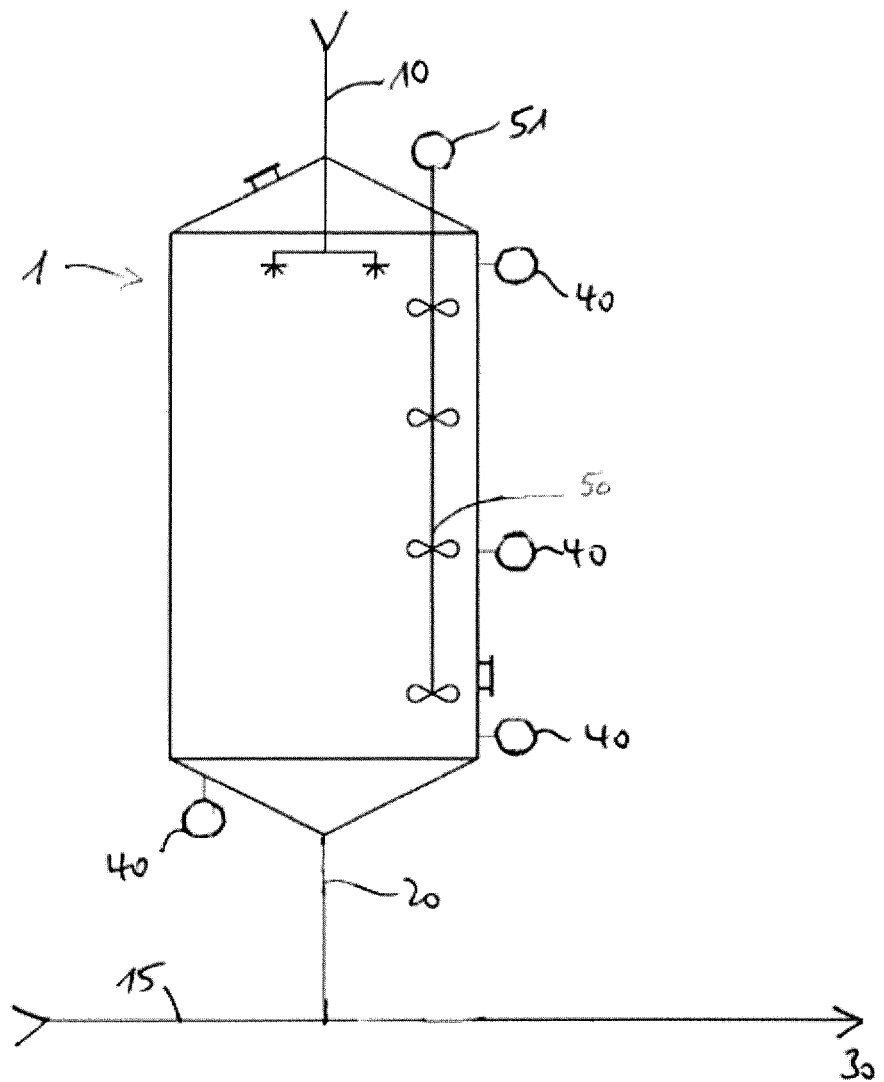

LARGE-SCALE, HIGH DENSITY STORAGE OF LARVAE

CROSS-REFERENCE TO RELATED APPLICATIONS

This application is the United States national phase of International Application No. PCT/EP2019/064673 filed Jun. 5, 2019, and claims priority to European Patent Application No. 18175908.5 filed Jun. 5, 2018, the disclosures of which are hereby incorporated by reference in their entirety.

BACKGROUND OF THE INVENTION

Field of the Invention

The invention generally relates to storing of live insect larvae in large quantities and in particular to prolonging the period of time without degeneration of the larvae.

Discussion of the Related Art

When using insects and their larvae as a food or feed source on an industrial scale, such as a source of protein, it is important to provide a possibility of storing them alive for an extended period of time, such as several, e.g. up to four days. During storing, care should be taken to avoid harming or causing pain to the insect larvae. Storing of the larvae allows for buffering insect larvae and/or building up a sufficient quantity of larvae to have a continuous stream for processing. The larvae might also be washed and rinsed of rearing residue and subsequently be prepared for further processing.

Previously, when storing a large quantity of live larvae, multiple smaller sized containers have been used. Containers that are used for breeding insects are, for example, described in WO 2015/023178 A1.

However, when storing live larvae, there is the problem that the larvae tend to cluster and the resulting inhomogeneous distribution may cause hot spots. These hot spots may cause degradation of the stored larvae since no efficient and uniform cooling is achieved. When a high density of larvae occurs due to the clustering, there is further the risk of crushing of the larvae due to their own weight. However, homogenizing the larvae in the containers is difficult to achieve. In addition, the growth of the larvae might also change their composition, making it difficult to achieve a consistent end product quality. Furthermore, it is very space-intensive to store a high quantity of insect-larvae using this kind of system.

CN 203467453 U and CN 103493789 A disclose large-sized cultivation and breeding tanks for mealworms, comprising a temperature and humidity sensing device and a stirring shaft with a plurality of stirring arms. The stirring arms have air holes, through which gases of different temperature and humidity can be provided to prevent mealworm larvae from dying due to oxygen deficiency, high temperature or low humidity.

Furthermore, it is known to preserve insect eggs by freezing them and defrosting them when needed. This technique is however not applicable for storing living insects or larvae.

There is thus the need for a method and device for prolonged storing of living insects or insect larvae that overcome the problems of known solutions. In particular, the present invention should prevent clustering of the stored larvae and prevent or slow down growth of microbial pathogens that might be present. The invention should further allow for placing the larvae in the system and continuously extracting them from the system without damaging the larvae. Furthermore, the metabolism of the insect larvae should be slowed down or even stopped in order to preserve the current status of the insect larvae, prevent quality degeneration and prepare the larvae for further processing.

These problems are solved with the method and the storage means defined by the invention.

SUMMARY OF THE INVENTION

In the description, the term tank is used to describe the storage means, but any container suitable for storing insect larvae together with a cooling medium is to be covered by this terminology. Also, in the following, water is used as an exemplary cooling medium without excluding any other cooling medium suitable for the purpose of the invention. The insect larvae to be treated preferably are black soldier fly larvae or meal worms. The insect larvae are preferably suitable for producing animal feed or food.

Instead of cold water, other means for cooling such as fluids different from water, solids, in particular ice, gases or any combination thereof may be introduced into the tank.

The present invention is based on the idea to store the larvae in water, wherein the amount of larvae in the water is controlled such that the tank volume is efficiently used but damage of the larvae may be avoided. The larvae inside the tank are homogenized to avoid clustering of the larvae inside the tank. By suitably controlling the water temperature, the larvae are metabolically deactivated and pathogens may be prevented from multiplying.

In particular, the invention encompasses a method for storing larvae by means of a storage tank. The storage tank may comprise an inlet, for introducing the water and/or the larvae. The tank further comprises a drainage, allowing for water and/or larvae to be drained from the tank. Water may be added to the tank via an inlet that is separate from the inlet of the larvae. Alternatively, the larvae may be introduced to the tank premixed with the desired amount of water, through a single inlet. Similarly, drainage of water and larvae may be done though separate outlets. Alternatively, the same outlet may be used to drain a water-larvae mixture, the larvae being separated from the water using appropriate means such as a mesh having openings that have a size to ensure proper separation while avoiding damage to the larvae.

The storage tank further comprises means for agitating the content of the storage tank, for example in the form of a stirring device or a mixing screw. The agitation can thereby by performed continuously or periodically or in an irregular manner. Other means might comprise pumping the water in circle, creating a jet that sets fluid in motion or putting the tank itself in motion. The method comprises maintaining the content of the storage tank at a temperature below 15° C., preferably 10° C. or even 7° C. for a long term storage (up to four days). The cooling medium is preferably liquid. In case of water, the temperature is thus preferably maintained above 0° C. When controlling the temperature to be below 7° C., the growth of pathogens can effectively be prevented. The method further comprises controlling the water-to-larvae ratio (by weight) to be between 30:70 to 80:20, preferably 50:50. The method further comprises agitating the content of the storage tank by said agitating means.

The temperature inside the storage tank may be controlled by maintaining a continuous water flow through the tank, the introduced water having the desired temperature or a lower temperature. In addition or alternatively, the tank may be actively cooled, in particular by providing a cooling means within and/or outside the tank. Furthermore, a continuous flow of air may be provided inside the storage tank.

Also, the invention encompasses a storage tank for storing insect larvae, in particular to be used with the method according to the invention. The storage tank may be aligned vertically or horizontally. The storage tank comprises an agitating mechanism to agitate the content of the storage tank, an inlet and an outlet for water and/or larvae. The storage tank is configured to cool the content to a temperature below 15° C., and to agitate the content by the agitating means.

When storing living insect-larvae, metabolic deactivation of the larvae has been found important since otherwise the animals would develop and require food which might lead to cannibalism. Furthermore, enzymes in the larvae's gut might destroy themselves when they die. Also, active larvae produce heat which deteriorates the storing performance.

Metabolic deactivation as well as inhibiting bacteria growth is achieved according to the present invention by cooling the water and the larvae therein to below a certain temperature. At a temperature below 15° C., the larvae are not metabolically active and therefore do not require food and evade the problems as explained above. Thus, by maintaining a temperature below 15° C., spoiling of the insect larvae can largely be prevented. By maintaining a temperature below 7° C., additionally growth of microbial pathogens is hindered.

There is however the additional problem that the animals tend to form clusters wherein the core of such a cluster might stay warm even when kept in cold water. Therefore, according to the present invention, the water-larvae mixture is agitated in some form in order to prevent clustering of the animals and ensure a homogenous cooling of the insect larvae. A further positive side effect thereof is that since the animals are floating in water, crushing due to their own weight on each other can also be prevented. Additionally, it makes extraction of the larvae easier and may prevent clogging of the pipes when sent to processing. Since insects tend to live in large groups on little space, an overcrowding problem will not arise when rearing and storing large amounts of insect larvae.

BRIEF DESCRIPTION OF THE DRAWINGS

The features, objects and advantages of the invention will be made apparent by the detailed description that follows and the figures wherein FIG. 1 schematically shows a storage tank according to the present invention.

DETAILED DESCRIPTION OF THE PREFERRED EMBODIMENTS

Insect larvae may be stored in tanks together with water. In recent years much thought has been put into storing insect larvae in large quantities for a long time period (up to 4 days) without degeneration and while maximising the output. However, there are a lot of problems to be faced when storing the insect larvae. For example, the enzymes in the larvae gut have to be kept from destroying the larvae itself when they die. Therefore, the system must either inactivate the enzymes or keep the larvae alive in such a way that they can control the enzymes.

A further problem that can occur is the contamination of the larvae by microbial pathogens since the bacteria might be harmful to the larvae. Also, high densities of stored larvae should be avoided since high density or clustering of larvae can result in large heat production which needs to be controlled to prolong the storing period, and further it might lead to crushing of the larvae due to their own weight.

Furthermore, the larvae should be metabolically deactivated. Otherwise they can develop or require food which might lead to cannibalism amongst themselves. Also, a large storing facility should be used in order to allow for buffering and therefore to have a continuous stream for processing.

According to the present invention, these problems can be solved by maintaining a homogenous distribution of insect larvae in the water-larvae mixture on the one hand and by maintaining a certain temperature on the other hand. According to the present invention, the water-insect larvae mixture is stirred and cooled to avoid clustering and to reduce the temperature of the insect larvae.

To achieve the above stated objects, a storage tank is provided. FIG. 1 shows an embodiment of a storage tank according to the present invention. Tank 1 is provided with a water inlet 10, an insect larvae inlet 15, a water and insect larvae drainage 20. The storage tank according to the invention is further provided with an agitation mechanism 50 driven by a motor 51 to stir the content thereof. In the embodiment shown in FIG. 1, separate inlets for water and larvae are provided. According to an alternative embodiment, a water-larvae mixture with the desired ratio may be prepared outside the tank and introduced into the tank via a single inlet. Similarly, separate outlets for larvae and water may be provided. In this case, the water outlet should be equipped with a separating means to ensure that no larvae leave the tank through the water discharge opening. The separating means can be e.g. a grid or any other kind of filtering means which may also be removable. The larvae, on the other hand, may be extracted together with a corresponding amount of water. After extraction, the larvae must be homogenized to prevent clogging of the pipes as they are sent to processing.

Water provided through the water inlet 10 is mixed with insect larvae provided through the insect larvae inlet 15 inside the storage tank 1. Thereby, the insect larvae are cooled to a temperature according to the water temperature. FIG. 1 shows cooling means 40 arranged at the outer surface of the storing tank that may be used to cool the content of the tank. In order to maintain the temperature of water-larvae mixture inside the tank, a continuous stream of cooled water at the desired temperature may flow through the tank. When maintaining the water at a temperature below 15° C., the insect larvae are not metabolically active and therefore do not require food and evade the problems as explained above. Thus, by maintaining a temperature below 15° C., degradation of the insect larvae can largely be prevented. By maintaining a temperature below 7° C., additionally growth of microbial pathogens is hindered. A preferred ratio of water to insect larvae (by weight) is between 30:70 to 80:20, in other words the amount of water in the mixture shall be 30-80% of the total weight. More preferably, an amount of 50% water and 50% insect larvae by weight is maintained.

As a further advantage, by storing the insect larvae in water, the effective weight thereof is reduced since they float, and crushing of the larvae due to high densities can thus be avoided.

If insect larvae begin to cluster, hot spots might arise since the core of a larvae group might stay warm which would counteract the aim of prolonging the storing period. In order to prevent the insect larvae from clogging and developing clusters that are more difficult to fully cool, an agitating mechanism 50 stirs the water-insect larvae mixture without damaging or harming the insect larvae. Once the insect larvae are completely cooled and metabolically deactivated, they cease to produce heat and agitation of the water-insect larvae mixture becomes redundant.

A further advantage of generating a homogenous mixture of water and insect larvae is that the insect larvae are much easier to extract. Specifically, in the embodiment shown in FIG. 1, the water-larvae mixture is extracted from the tank through piping 20 to outlet 30 towards downstream processing.

The storage tank is preferably large in order to be able to buffer insect larvae and build up a sufficient quantity of larvae to have a continuous stream for processing. The storage tank preferably is aligned vertically to minimise the necessary floor space but may be aligned horizontally, e.g. for transportation on a truck or the like.

The present invention allows for large scale, high density storage of insect larvae. Homogenization of the larvae allows avoiding hot spots by clustering of larvae. This also ensures the homogenous outtake of larvae towards the downstream process.

The invention claimed is:

1. A method for storing living insect larvae in water, comprising
   providing a mixture of insect larvae and water to a storage tank,
   controlling the amount of the water in the mixture of the storage tank to be between 30% and 80% of the total weight of said mixture,
   maintaining the mixture of the storage tank at a temperature below 10° C. by at least one of the following: (a) introducing a continuous water flow through the storage tank; and (b) introducing a continuous flow of air inside the storage tank, and agitating
   the mixture of the storage tank.

2. The method according to claim 1, wherein the temperature inside the storage tank is maintained below 7° C.

3. The method according to claim 1, wherein the temperature inside the storage tank is controlled by providing a continuous flow of the water at the desired temperature through the storage tank.

4. The method according to claim 1, wherein a continuous air flow inside the storage tank is provided.

5. The method according to claim 1, further comprising draining the mixture of insect larvae and the water from the storage tank.

6. The method according to claim 5, further comprising separating the larvae from the water and processing of the insect larvae.

7. The method according to claim 1, wherein the agitation is performed continuously, periodically or in an irregular manner.

8. The method according to claim 1, wherein the agitating step is carried out by a mixing screw.

* * * * *